United States Patent
Woodcraft

(10) Patent No.: US 8,466,313 B2
(45) Date of Patent: Jun. 18, 2013

(54) FLUORIDATION OF IODONIUM SALTS

(75) Inventor: John Woodcraft, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 234 days.

(21) Appl. No.: 13/058,338

(22) PCT Filed: Aug. 13, 2009

(86) PCT No.: PCT/EP2009/060523
§ 371 (c)(1),
(2), (4) Date: Feb. 10, 2011

(87) PCT Pub. No.: WO2010/018218
PCT Pub. Date: Feb. 18, 2010

(65) Prior Publication Data
US 2011/0144344 A1    Jun. 16, 2011

Related U.S. Application Data

(60) Provisional application No. 61/088,736, filed on Aug. 14, 2008.

(30) Foreign Application Priority Data

Aug. 14, 2008  (GB) .................................. 0814893.4

(51) Int. Cl.
*C07C 229/00* (2006.01)

(52) U.S. Cl.
USPC ......................................................... 562/446

(58) Field of Classification Search
None
See application file for complete search history.

(56) References Cited

FOREIGN PATENT DOCUMENTS

WO    2005/061415    7/2007
WO    2007/141529    12/2007

OTHER PUBLICATIONS

Carroll, et.al. "Radical Scavengers: A Practical Solution to the Reproducibility Issue in the Fluorination of Diaryliodonium Salts" J. of Fluorine Chemistry, Vol. 128, 2007, pp. 127-132.
GB08014893.4 Search Report Dated Dec. 4, 2008.
PCT/EP2009/060523 ISRWO Dated Feb. 18, 2010.

*Primary Examiner* — Johann R Richter
*Assistant Examiner* — Jennifer C Sawyer

(57) ABSTRACT

The present invention provides an improved method for fluoridation of an iodonium salt wherein a solution of the iodonium salt comprising a free radical trap is stored before the reaction is carried out. The method of the invention may be automated, which is particularly convenient when the method of the invention is radiofluoridation. As such the present invention also provides a cassette comprising the iodonium salt solution suitable for carrying out the method of the invention on an automated synthesizer.

13 Claims, No Drawings

FLUORIDATION OF IODONIUM SALTS

This application is a filing under 35 U.S.C. 371 of international application number PCT/EP2009/060523, filed Aug. 13, 2009, which claims priority to Great Britain application number 0814893.4 filed Aug. 14, 2008 and U.S. application No. 61/088,736 filed Aug. 14, 2008, the entire disclosure of each of which is hereby incorporated by reference.

TECHNICAL FIELD OF THE INVENTION

The present invention relates to iodonium salt fluoridation. Specifically, the present invention relates to a method for the fluoridation of an iodonium salt wherein the reaction is carried out following storage of a solution of said iodonium salt. The invention is also particularly suitable for carrying out radiofluoridation of said iodonium salt. The radiofluoridated compound obtained by the method of the invention is useful for inclusion in pharmaceutical compositions, e.g. for use in positron emission tomography (PET) imaging. Furthermore, the invention relates to a kit for the facile performance of the method of the invention as well as a cassette for the automated performance of the method of the invention.

DESCRIPTION OF RELATED ART

Nucleophilic substitution by fluoride is regarded as one of the most attractive ways to introduce fluorine into an organic compound. Aromatic nucleophilic substitution using the [$^{18}$F] fluoride anion to displace a suitable leaving group from an electron deficient aromatic ring is a well-known known method for the production of [$^{18}$F] fluoroarenes. The nucleophilic substitution reaction is illustrated below:

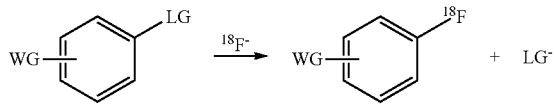

wherein WG represents between 1 and 4 electron withdrawing groups and LG represents a suitable leaving group, e.g. fluoro, bromo, nitro, tertiary amino or iodo.

WO 2005/061415 identifies that decomposition of iodonium salts by a free radical chain reaction process is a significant factor in the observed yield variability (reported e.g. by Pike et al J. Chem. Soc. Chem. Comm. 1995: 2215-16) of radiofluoridation reactions using iodonium salts. The inclusion of a free radical trap in the reaction mixture was demonstrated in WO 2005/061415 to block the radical chain decomposition pathway for iodonium salts such that the reaction leading to radiofluoridation occurs preferentially and the yield of the desired radiofluorinated product becomes reproducible. In the experiments described therein, a free radical trap is introduced to the iodonium salt as the fluoridation reaction is being carried out (see experimental examples of WO 2005/061415). RCY's of around 40-60% were consistently obtained when the reaction took place in the presence of a radical trap.

[$^{18}$F]-labelled compounds comprising a [$^{18}$F]-fluoroalkenyl group have also been synthesised using iodonium salt chemistry analogous to that described for obtaining [$^{18}$F]-fluoroarenes (WO 2007/073200). Inclusion of a free radical trap in the reaction mixture was also reported in this patent application.

In another report, Carroll et al (J. Fluorine Chem. 2007; 128. 127-132) demonstrate that inclusion of radical scavengers in the fluoridation of diaryliodonium salts significantly improved the reproducibility of the process and the material yield of the desired fluoroarene compounds. In the methods described therein, the radical scavenger is brought together with the diaryliodonium salt in the reaction vessel (see Experimental sections 4.3, 4.5, and 4.6 of Carroll et al).

Clearly, addition of a radical trap results in improved yields in the fluoridation of iodonium salts. Applicant believes that there is scope to further improve the yields of these reactions.

SUMMARY OF THE INVENTION

The present invention provides a method for fluoridation of an iodonium salt wherein a solution of the iodonium salt comprising a free radical trap is stored before the reaction is carried out. The method of the invention surprisingly results in increased yields of the desired fluorinated product. Furthermore, the ability to store the iodonium salt solution conveniently enables provision of a pre-prepared solution for use in the method of the invention. The present invention also provides a kit comprising the iodonium salt solution in a suitable container for storage. A cassette is also provided which is suitable for carrying out the method of the invention on an automated synthesiser. In contrast to presently-known methods for fluoridation of iodonium salts where automation would require separate vials for solid iodonium salt and for solvent, the method of the present invention permits both to be advantageously contained in a single vial. The automated method of the invention is particularly convenient when the method of the invention is radiofluoridation.

DETAILED DESCRIPTION OF THE INVENTION

In one aspect, the present invention relates to a method for the synthesis of a fluorine-labelled compound, said method comprising:

(a) providing an iodonium salt solution, wherein said solution comprises (i) an iodonium salt, or a protected version thereof and, (ii) a free radical trap, wherein (i) and (ii) are dissolved in an organic solvent;

(b) storing said solution of step (a) in a storage container for a storage period of at least 3 hours, at a storage temperature which is above the freezing point of said solution and which is less than or equal to 30° C.;

(c) following said storing step (b), treating said solution with a fluoride ion source to generate said fluorine-labelled compound.

The "fluorine-labelled compound" of the method of the invention is a chemical compound whose chemical formula includes at least one fluorine atom, wherein the term "fluorine atom" encompasses both non-radioactive and radioactive isotopes of fluorine. In a preferred embodiment of the method of the invention, the fluorine atom is the radioactive isotope $^{18}$F. Preferably, the fluorine-labelled compound of the method of the invention is of the general formula Q-F, wherein Q is as defined below for Formula I, and F represents the fluorine atom.

The "iodonium salt solution" of the method of the invention comprises an iodonium salt. The term "iodonium salt" is defined in the present invention as a compound comprising an ion of the form $Y_2I^+$. Suitably, the iodonium salt is present in the iodonium salt solution at a concentration of between 0.001-0.1M, preferably 0.01-0.05M, and most preferably 0.01-0.02M. Preferred iodonium salts are described in more detail below.

The iodonium salt solution also comprises a free radical trap. The term "free radical trap" is defined herein as any agent that interacts with free radicals and inactivates them. A suitable free radical trap in the method of the invention is selected from 4-aminobenzoic acid, 2,6-di-tert-butyl-4-methylphenol (BHT), 1,2-diphenylethylene (DPE), galvinoxyl, gentisic acid, hydroquinone, 2,2,6,6-Tetramethylpiperidine-N-Oxide (TEMPO), thiophenol, ascorbate, para-amino benzoic acid (PABA), β-carotene and DL-α-tocopherol. Preferred free radical traps for use in the method of the invention are TEMPO and DPE, with TEMPO being most preferred. The iodonium salt solution usually contains at least 1 mole percent of the free radical trap and preferably about 2-500 mole percent. A more preferred range is from about 10 to 400 mole percent of free radical trap in the solution.

A suitable "organic solvent" for the iodonium salt solution may be selected from acetonitrile (ACN), dimethylformamide (DMF), dimethylsulphoxide (DMSO), dimethylacetamide (DMAC), tetrahydrofuran (THF), dioxan, 1,2 dimethoxyethane (DME), sulpholane, or N-methylpyrrolidininone. Preferred organic solvents herein are ACN, DMF, DMSO, DMAC, and THF, most preferably ACN, DMF, and DMSO. The organic solvent is preferably degassed prior to use, a step that is carried out e.g. by bubbling nitrogen or argon through the gas for a period of around a few minutes. In a most preferred embodiment, the organic solvent is "dry", meaning that the level of water present is 1000 ppm or less, more suitably 600 ppm or less, and preferably 100 ppm or less. This is preferred because reactivity of the fluoride ion with the iodonium salt in the treating step is enhanced when the reaction is carried out with a dry solvent, and it is convenient to carry out the treating step using the stored iodonium salt solution without further manipulation.

A suitable "storage container" for storage of the iodonium salt solution is one which does not interact with any components of the synthesis reaction, optionally permits maintenance of sterile integrity, plus optionally allows for an inert headspace gas (e.g. nitrogen or argon), whilst also optionally permitting addition and withdrawal of solutions by syringe. Such storage containers are preferably liquid-tight or gas-tight jars, flasks, ampoules and vials, the seal being provided by a liquid-tight or gas-tight closure such as a lid, stopper, or septum. A most preferred such storage container is a septum-sealed vial, wherein the gas-tight closure is crimped on with an overseal (typically of aluminium). Such storage containers have the additional advantage that the closure can withstand vacuum if desired, e.g. to change the headspace gas or degas solutions and can withstand an overpressure, e.g. to aid in the removal of the solution from the container. The iodonium salt solution is preferably stored in the dark. More specifically it is preferred that UV light is specifically excluded, because it is believed that free-radical degradation of the iodonium salt in solution is stimulated by UV light. For example, the storage container may be made of brown glass, or the storage container may be wrapped with aluminium foil during storage.

Treatment of the iodonium salt solution with a fluoride ion source, also known as "fluoridation", may be effected in the presence of either (i) an organic solvent of the type described above for the iodonium salt solution, or (ii) an ionic liquid such as an imidazolium derivative (e.g. 1-ethyl-3-methylimidazolium hexafluorophosphate), a pyridinium derivative (e.g., 1-butyl-4-methylpyridinium tetrafluoroborate), a phosphonium compound, or tetralkylammonium compound. The treating step of the method of the invention is suitably carried out at a non-extreme temperature, e.g., 15° C. to 180° C., preferably at the higher end of the range, e.g. from 80° C. to 150° C., and particularly at or around 120° C. In a preferred embodiment, the organic solvent selected for fluoridation is most conveniently the same organic solvent used for storage of the iodonium salt solution. It will be appreciated by the skilled person that some of the temperatures described herein for carrying out the fluoridation reaction exceed the boiling point of the organic solvent. In a preferred embodiment therefore, the reaction vessel is sealed so that the pressure increases with the rising temperature and consequently raises the boiling point. For example, acetonitrile boils about 80° C. but reactions are possible in a sealed vessel at 120° C. without boiling of acetonitrile.

The choice of reaction vessel for carrying out the fluoridation reaction will depend on the nature and quantity of reactants used. Suitable reaction vessels are made from materials that allow the desired reaction to progress without interference. Such reaction vessels include standard laboratory glassware such as beakers and flasks, as well as cartridges for automated synthesis and microfabricated vessels, all of which are familiar to those of skill in the art.

While it is possible to successfully carry out the fluoridation reaction of step (c) where the reaction solvent comprises water (WO 2005/097713), it is generally believed that reactivity of the fluoride ion is increased, and hydroxylated by-products resulting from the presence of water are avoided, when water is removed from fluoride prior to the reaction. Fluoridation reactions are commonly carried out using anhydrous reaction solvents (Aigbirhio et al J. Fluor. Chem. 1995; 70: 279-87). The removal of water from the fluoride ion is referred to as making "naked" fluoride ion and is intended to increase the reactivity of the fluoride ion as well as to avoid hydroxylated by-products resulting from the presence of water (Moughamir et al Tett. Letts. 1998; 39: 7305-6). Therefore, in one embodiment, the solvent used for fluoridation is "dry", as defined previously herein.

A further step typically used in the art to improve the reactivity of fluoride ion for fluoridation reactions is to add a cationic counterion prior to the removal of water. The counterion should possess sufficient solubility within the anhydrous reaction solvent to maintain the solubility of the fluoride ion. Therefore, counterions that have been used include large but soft metal ions such as rubidium or caesium, potassium complexed with a cryptand such as Kryptofix™, or tetraalkylammonium salts. A preferred counterion for fluoridation reactions is potassium complexed with a cryptand such as Kryptofix™ because of its good solubility in anhydrous solvents and enhanced fluoride reactivity. The "fluoride ion source" of the present invention is suitably selected from potassium fluoride, caesium fluoride and tetraalkylammonium fluoride. The preferred fluoride ion source of the invention is potassium fluoride activated with Kryptofix™ Most reagents described in this paragraph are available from chemical suppliers such as Sigma Aldrich. Tetraalkylammonium salts can be obtained from ABX Chemicals.

A preferred iodonium salt of the method of the invention is a compound of Formula I:

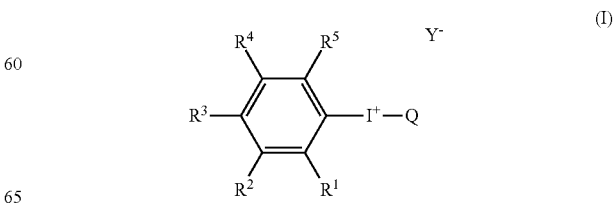

wherein:
each of $R^1$-$R^5$ is an R group independently selected from hydrogen, nitro, cyano, halo, $C_{1-10}$ hydroxyalkyl, $C_{2-10}$ carboxyalkyl, $C_{1-10}$ alkyl, $C_{2-10}$ alkoxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, or $C_{2-10}$ carbamyl, or protected versions of any of these groups; or two adjacent R groups, together with the carbon atoms to which they are attached, form a four- to six-membered ring, or protected versions thereof;

Q represents either a $C_{5-14}$ aryl, or a $C_{4-13}$ heteroaryl group, optionally attached to $I^+$ via a $C_{2-6}$ alkenylene group, wherein Q has 0 to 3 $R^6$ substituents, wherein each $R^6$ is an R* group selected from:
halo, cyano, nitro, —C(═O), -E, —OE, —OC(O)E, —C(═O)OE, —SO$_2$E, —SE, —NE$_2$, —C(═O)NE$_2$, —N(E)COE; wherein E at each occurrence is selected from hydrogen, $C_{1-6}$ alkyl, $C_{1-5}$ heteroalkyl, $C_{2-6}$ alkenyl, $C_{2-6}$ alkynyl, $C_{1-6}$ alkoxyalkyl, $C_{1-6}$ haloalkyl, $C_{2-6}$ haloalkenyl, $C_{2-6}$ haloalkynyl, $C_{1-6}$ haloalkoxy-$C_{1-6}$ alkyl, $C_{4-12}$ cycloalkyl, $C_{4-12}$ heterocycloalkyl, $C_{5-12}$ aryl, and a $C_{4-13}$ heteroaryl group;
and protected versions of any of these R* groups;
with the proviso that R* is not hydrogen;
wherein any two adjacent hydrocarbyl R* groups together with the carbons to which they are attached may form a 4- to 6-membered ring;
and wherein any of these R* groups may be attached to Q via $C_{1-6}$ alkylene;
and wherein any hydrocarbyl $R^6$ group is optionally substituted by one or more
$R^7$ groups, and any hydrocarbyl $R^7$ group is optionally substituted with one or more $R^8$ groups, wherein $R^7$ and $R^8$ are both an R* group; and, Y⁻ is an anion, suitably selected from trifluoromethane sulphonate (triflate), methane sulphonate (mesylate), trifluoroacetate, toluene sulphonate (tosylate) and perfluoro $C_2$-$C_{10}$ alkyl sulphonate.

"Alkyl", used either alone or as part of another group, is defined herein as any straight or branched saturated or unsaturated $C_nH_{2n+1}$ group, wherein unless otherwise specified n is an integer between 1 and 10. Alkyl groups include e.g. methyl, ethyl, propyl, isopropyl, butyl, isobutyl, t-butyl, 1-methylpropyl, pentyl, isopentyl, sec-pentyl, hexyl, heptyl, and octyl.

The term "cycloalkyl" is any cyclic alkyl wherein n of $C_nH_{2n}+_1$, unless otherwise specified, is an integer between 3 and 10. Examples of cycloalkyl groups include cyclopropyl, cyclobutyl, cyclopentyl, and cyclohexyl.

"Aryl" is defined herein as any mono-, bi- or tri-cyclic $C_{5-14}$ molecular fragment or group comprising at least one aromatic ring, and preferably having 5 to 6 ring members in each ring. Aryl groups include purely aromatic radicals such as phenyl, naphthyl, tetrahydronaphthyl, indane, and biphenyl, as well as radicals comprising at least one aromatic ring fused with one or more cycloalkyl or heterocycloalkyl rings.

The terms "heteroalkyl", "heterocycloalkyl", and "heteroaryl" as defined herein are, respectively, an alkyl, a cycloalkyl or an aryl as defined above, wherein at least one atom in the chain is a heteroatom selected from N, S or O.

"Alkoxyalkyl" is a $C_{2-10}$ straight chain or branched alkyl group with a terminal oxygen linking the alkyl group to the rest of the molecule. Alkoxyalkyl includes methoxy, ethoxy, propoxy, isopropoxy, butoxy, t-butoxy, pentoxy and so on.

"Carboalkoxy" embraces alkoxyalkyl radicals, as defined above, attached to one of two unshared bonds in a carbonyl group, wherein a "carbonyl" group is a functional group composed of a carbon atom double-bonded to an oxygen atom, i.e. C═O.

The term "alkenyl" refers to an acyclic hydrocarbon radical containing at least one double bond. Such alkenyl radicals contain from 2 to 10 carbon atoms, preferably 2 to 8 carbon atoms and more preferably 2 to 6 carbon atoms. Examples of suitable alkenyl radicals include propenyl, buten-1-yl, isobutenyl, penten-1-yl, 2-2-methylbuten-1-yl, 3-methylbuten-1-yl, hexen-1-yl, hepten-1-yl, and octen-1-yl. The term "alkenylaryl" is used herein to refer to a $C_{7-20}$ group consisting of an alkenyl group as defined herein linked to an aryl group as defined herein, e.g. phenyl-butenyl, and phenyl-pentenyl. An "alkenylheteroaryl" is an alkenylaryl group comprising one or more heteroatoms in the aryl moiety, wherein said heteroatoms are selected from N, S and O.

The term "alkynyl" refers to an acyclic hydrocarbon radical containing one or more triple bonds, such radicals containing from 2 to 10 carbon atoms, preferably having 2 to 8 carbon atoms and more preferably 2 to 6 carbon atoms. Examples of alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl. The term "alkynylaryl" is used herein to refer to a $C_{7-20}$ radical consisting of an alkynyl group as defined herein linked to an aryl group as defined herein.

"Acyl" means —CO-alkyl wherein alkyl is as defined above.

"Aroyl" means an —CO-aryl group wherein the aryl group is as defined above. Exemplary groups include benzoyl and 1- and 2-naphthoyl.

"Carbamyl" means the radical —C(O)NH$_2$, wherein one or both hydrogens may be substituted with an alkyl or an aryl group, as defined above.

The term "nitro" refers to —NO$_2$.

The term "cyano" refers to —CN.

The term "halo" means a halogen substituent selected from fluorine, chlorine, bromine, and iodine, including isotopes thereof. The terms "haloalkyl", "haloalkenyl" and "haloalkoxy" represent alkyl, alkenyl and alkoxy groups, respectively, as defined herein, substituted with one or more halo groups.

The term "hydrocarbyl" refers to a radical which primarily comprises carbon and hydrogen atoms. A hydrocarbyl group may for example be alkyl, cycloalkyl, aryl, alkoxyalkyl, carboalkoxy, alkenyl, alkenylaryl, alkenylheteroaryl, alkynyl, acyl, aroyl, or carbamyl, all of which are defined above.

To obtain a "protected version" of any R or R* group defined herein, standard methods of protecting group chemistry are employed. After the fluoridation is complete, any protecting groups may be removed by simple procedures which are also standard in the art. By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection, the desired in vivo imaging agent is obtained. Protecting groups, are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. For thiol groups, suitable protecting groups are: trityl and 4-methoxybenzyl. Suitable protection and deprotection methodologies may be found, e.g., in Protecting Groups in Organic Synthesis, Theodora W. Greene and Peter G. M. Wuts, published by John Wiley & Sons Inc (1999).

$R^1$ to $R^5$ are most suitably each hydrogen. In another embodiment, one of the groups $R^1$ to $R^5$ (e.g. the group $R^3$) is $C_{1-10}$ alkoxy, such as methoxy, and the others are each hydrogen.

A preferred Q group is either a $C_{5-14}$ aryl, or a $C_{4-13}$ heteroaryl group. Most preferred are monocyclic aryl or heteroaryl groups including phenyl, pyridyl, pyrazolyl, bicyclic aryl or heteroaryl groups including naphthalyl, quinolinyl, or tricyclic aryl or heteroaryl groups wherein at least one aryl or heteroaryl group is fused with a cycloalkyl group. For heteroaryls, a preferred heteroatom is N.

Preferred $R^{6-8}$ groups include —C(═O), hydroxyl, $NH_2$, $C_{1-6}$ alkyl, —$SO_2$—$C_{1-6}$ alkyl, $C_{1-6}$ cycloalkyl, $C_{1-6}$ heteroalkyl, $C_{1-6}$ alkoxyalkyl, $C_{5-14}$ aryl, and $C_{4-13}$ heteroaryl, wherein any heteroatoms are preferably N or O and most preferably N.

Prior art methods for the synthesis and fluoridation of iodonium salts of Formula I are presented by Carroll et al (J. Fluorine Chem. 2007; 128: 127-132), as well as in WO 2005/061415 and WO 2007/141529.

The iodonium salt of the invention may alternatively be solid support-bound, as in Formula Ia:

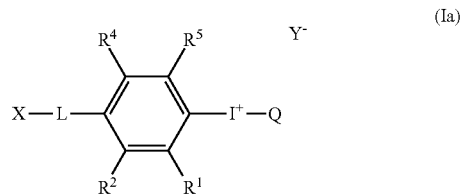

(Ia)

$R^1$, $R^2$, $R^4$, $R^5$, and Q are as defined above for Formula I;
L is a polyethylene glycol linker, or L comprises one to four $C_{5-12}$ arylene groups and/or $C_{1-20}$ alkylene, $C_{2-20}$ alkoxyalkylene or $C_{1-20}$ haloalkylene, and optionally one or more additional substituents such as C(═O), halogen, amide or sulphonamide; and,
X is any suitable solid-phase support which is insoluble in solvents used in the method and to which the linker L is covalently bound.

The term "alkylene" means a linear saturated divalent hydrocarbon moiety of 1-20 carbon atoms or a branched saturated divalent hydrocarbon moiety.

The term "arylene" refers to a $C_{5-12}$ aromatic divalent hydrocarbon moiety.

"Alkoxyalkylene" is an alkylene group as defined above which further comprises an oxygen atom in the chain, i.e. an ether linkage.

"Haloalkylene" is an alkylene group as defined above which is substituted with one or more halo groups, wherein halo is as defined above.

A suitable solid support X may be selected from polymers such as polystyrene (which may be block grafted, e.g. with polyethylene glycol), polyacrylamide or polypropylene, or glass or silicon coated with such a polymer. The solid support may be in the form of small discrete particles such as beads or pins, or as a coating on the inner surface of a cartridge or microfabricated vessel.

The function of the linker L is to space the reactive site sufficiently far from the solid support structure so as to maximise reactivity.

Examples of such linkers and solid supports are well known to those skilled in the art of to solid-phase chemistry, e.g. as described in Florencio Zaragoza Dorwald "Organic Synthesis on Solid Phase: Supports, Linkers, Reactions" Wiley-VCH (2000). Examples of the synthesis and fluoridation of a number of solid-phase bound iodonium salts of Formula Ia of the present invention are described in the experimental section of WO 2005/061415.

According to the current knowledge of the skilled person, an iodonium salt solution for use in a fluoridation reaction would be prepared with the intention to use the solution immediately upon, or very soon after, its preparation (see e.g. Experimental section of Carroll et al 3. Fluorine Chem. 2007; 128: 127-132). The present inventors unexpectedly observed that storing the iodonium salt solution prior to treating with a fluoride ion source permitted successful synthesis of the desired fluorine-labelled compound. In fact, the yields were observed to be, increased following storage in comparison to using the iodonium salt solution as defined herein immediately after preparation. This observation was surprising as the conventional wisdom in the art is that degradation of the components of a solution would be expected to take place during storage, thereby resulting in reduced yields of the desired product.

The temperature of storage of the iodonium salt solution is suitably above the freezing point of said solution, and less than or equal to 30° C. For any given liquid, the "freezing point" is the temperature at which the liquid changes state from a liquid to a solid. The temperature remains at this point until all the liquid has solidified. It is invariable under similar conditions of pressure, e.g., the freezing point of water under standard atmospheric pressure is 0° C. In the context of the present invention, the freezing point of a liquid is to be taken as the freezing point under standard atmospheric pressure. It is to be understood that "above the freezing point" is any temperature at or above the minimum temperature at which the liquid is entirely in the liquid state. In the method of the present invention, a preferred temperature range for storage of the iodonium salt solution is between 1 and 30° C., most preferably between 1 and 25° C., especially preferably between 1 and 20° C., most especially preferably between 1 and 10° C., and ideally between 1 and 5° C. A temperature of between 1 and 5° C. is the typical temperature range for refrigeration and is therefore easily accessible.

The skilled person would anticipate that longer storage periods are achievable where the storage temperature is lower. A longer storage period is desirable where the iodonium salt solution is manufactured centrally, and then shipped to customers. A preferred storage period is between 12 hours and 3 months, most preferably between 1 day and 1 month, especially preferably between 1-7 days, and most especially preferably between 3-5 days.

Storage for a period of between 3-5 days under standard refrigeration conditions has been demonstrated herein to significantly increase the yield of the desired product on treatment of the solution with a fluoride ion source. This is illustrated in Examples 2 and 3, which describe the synthesis of fluoridated compounds according to the method of the invention.

In a preferred embodiment, the method of the invention is carried out wherein the fluoride ion source is a [$^{18}$F]-fluoride ion source. In this case, the radiochemistry is performed using a nucleophilic radiofluorinating agent such as [$^{18}$F] caesium fluoride or [$^{18}$F] potassium fluoride. These radiofluorinating agents are prepared from cyclotron-produced no carrier added (NCA) [$^{18}$F] fluoride (as described by Aigbirhio et al J Fluorine Chem 1995; 70: 279).

[$^{18}$F]-fluoride ion is typically obtained as an aqueous solution which is a product of the irradiation of an [$^{18}$O]-water target. Conventional practice is to carry out various steps to convert [$^{18}$F]-fluoride into a reactive nucleophilic reagent, such that it is suitable for use in nucleophilic radiolabelling reactions. As with non-radioactive fluoridations, and as discussed earlier, these steps include the elimination of water from [$^{18}$F]-fluoride ion and the provision of a suitable counterion ("Handbook of Radiopharmaceuticals" 2003; Welch & Redvanly eds.; ch. 6: 195-227). Nucleophilic radiofluorination reactions are then carried out using anhydrous solvents (Aigbirhio et al J. Fluor. Chem. 1995; 70: 279-87).

Most preferably, the [$^{18}$F]-labelled compound is an [$^{18}$F]-labelled radiotracer, i.e. an [$^{18}$F]-labelled compound that following administration binds to a particular biological target within a subject, and is detectable using positron emission tomography (PET) imaging. To be suitable for mammalian administration, the [$^{18}$F]-labelled-radiotracer is comprised in a pharmaceutical composition. A "pharmaceutical composition" is defined in the present invention as a formulation comprising the [$^{18}$F]-labelled-radiotracer of the invention or a salt thereof in a form suitable for administration to humans. The pharmaceutical composition may be administered parenterally, i.e. by injection, and is most preferably an aqueous solution. Such a composition may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid). The method of the invention may further comprise the steps required to obtain a pharmaceutical composition, e.g. removal of organic solvent, addition of a biocompatible buffer and optional further ingredients as mentioned above. For parenteral administration, steps to ensure that the pharmaceutical composition is sterile and apyrogenic also need to be taken.

Where the method of the invention is a radiofluoridation method, particularly for the production of an [$^{18}$F]-labelled radiotracer, it may further comprise one or more of the following steps in any order:

(i) removal of excess $^{18}$F, for example by ion-exchange chromatography; and/or
(ii) removal of any protecting groups; and/or
(iii) removal of organic solvent; and/or
(iv) formulation of the resultant [$^{18}$F]-labelled compound as an aqueous solution; and/or
(v) sterilisation of the formulation of step (iv)

Non-limiting examples of some [$^{18}$F]-labelled radiotracers that may be prepared by the method of the invention wherein the iodonium salt is of Formula I are listed in Table 1, below. The respective -Q groups of iodonium salts of Formula I are given in the right hand column of Table 1, wherein in each case $P^1$-$P^4$ independently represent hydrogen or a protecting group.

TABLE 1

Examples of [$^{18}$F]-labelled radiotracers obtainable by the method of the present invention and their respective Q groups in Formula I

| $^{18}$F Compound | ----Q |
|---|---|
| 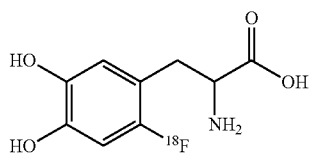<br>(a) [$^{18}$F]-FDOPA | 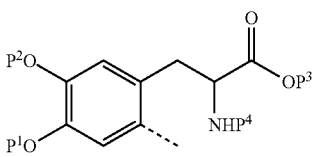 |
| 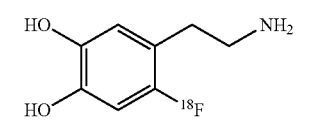<br>(b) [$^{18}$F]-dopamine | 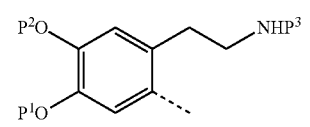 |
| 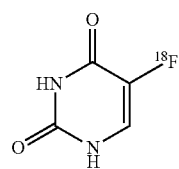<br>(c) [$^{18}$F]-5-fluorouracil | 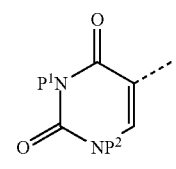 |

TABLE 1-continued

Examples of [$^{18}$F]-labelled radiotracers obtainable by the method of the present invention and their respective Q groups in Formula I

| $^{18}$F Compound | ----Q |
|---|---|
| (d) [$^{18}$F]-mFBG | |
| (e) [$^{18}$F]-FIBG | |
| (f) [$^{18}$F]-fluorocarazolol | |
| (g) [$^{18}$F]-pmPPF | |
| (h) [$^{18}$F]-altanaserine | |

TABLE 1-continued
Examples of [¹⁸F]-labelled radiotracers obtainable by the method of the present invention and their respective Q groups in Formula I
| ¹⁸F Compound | ----Q |
|---|---|
| 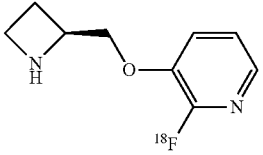 (i) [¹⁸F]-2-A85380 | 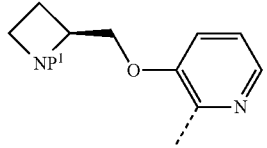 |
| 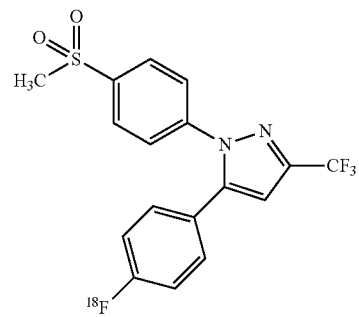 (j) [¹⁸F]-SC58125 | 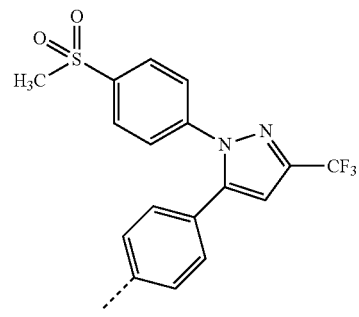 |
| 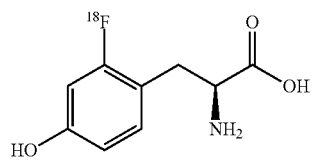 (k) [¹⁸F]-Tyrosine | 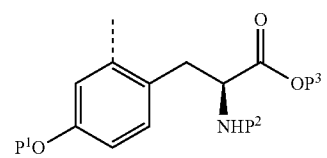 |
| 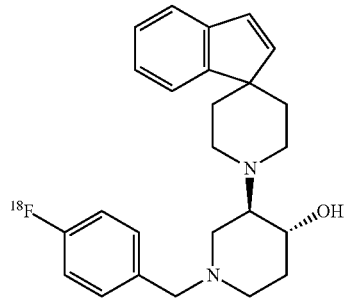 (l) [¹⁸F]-Spiro-FBT | 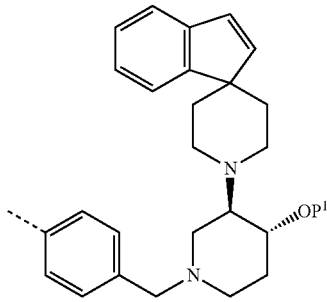 |
| 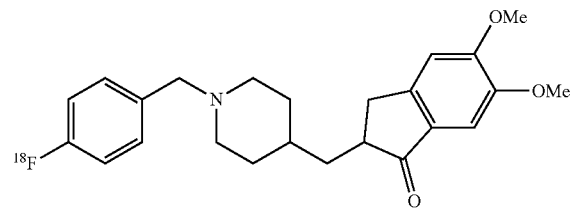 (m) [¹⁸F]-FDP | 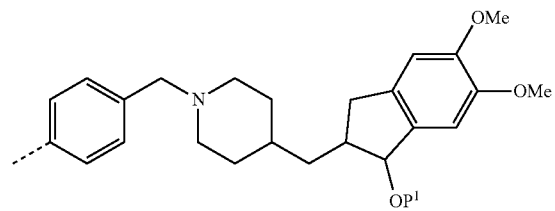 |

TABLE 1-continued
Examples of [$^{18}$F]-labelled radiotracers obtainable by the method of the present invention and their respective Q groups in Formula I
| $^{18}$F Compound | ----Q |
|---|---|
| 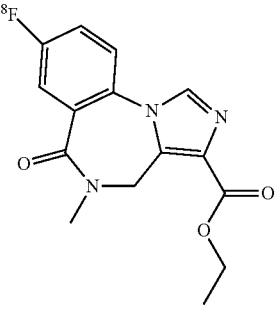 (n) [$^{18}$F]-flumanezil | 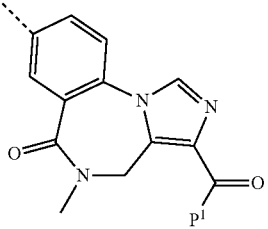 |
| 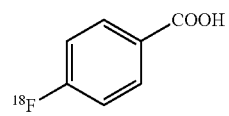 (o) [$^{18}$F]-SFB labelling agent | 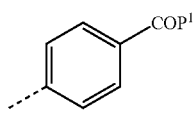 |
| 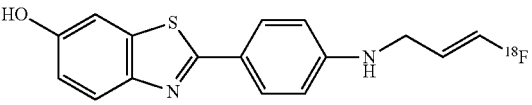 (p) 2-[4-((E)-3-[$^{18}$F]-Fluoro-allylamino)-phenyl]-benzothiazol-6-ol | 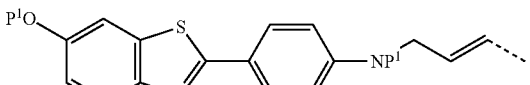 |
| 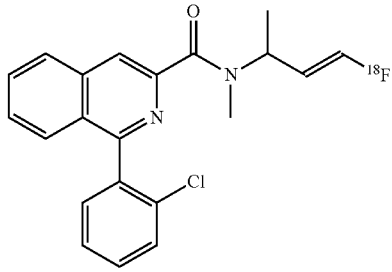 (q) 1-(2-chlorophenyl)-N-methyl-N-([$^{18}$F]-Fluoro-1-methyl-allyl)-3-isoquinolinecarboxyamide | 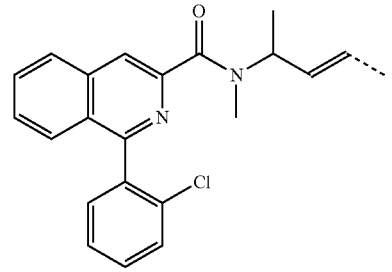 |
| 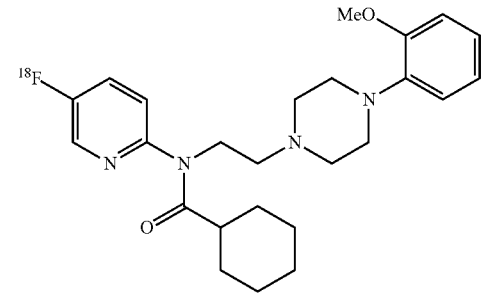 (r) [5-[$^{18}$F]-fluoro]-WAY-100635 | 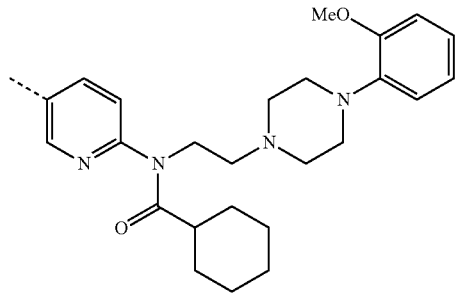 |

TABLE 1-continued

Examples of [$^{18}$F]-labelled radiotracers obtainable by the method of the present invention and their respective Q groups in Formula I

| $^{18}$F Compound | ----Q |
|---|---|
| 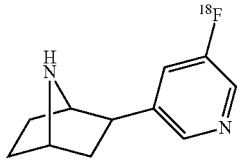<br>(s) Nor-chloro[$^{18}$F]epibatidine | 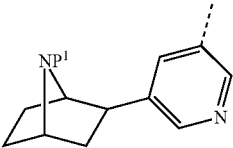 |
| 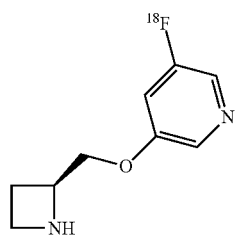<br>(t) 3-[$^{18}$F]fluoro-A-85380 | 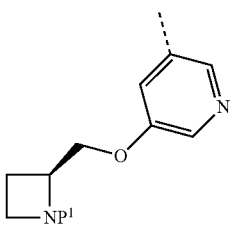 |
| 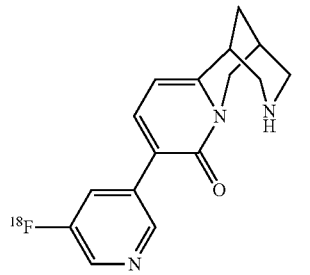<br>(u) (-)-(9)-(3-[18F]fluoropyridinyl)cystisine | 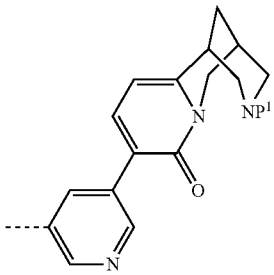 |

When the fluorine-labelled compound of the method of the invention is a [$^{18}$F]-radiotracer, e.g. any of the compounds shown above in Table 1, the radiotracer is useful in a method for obtaining an image of a patient, the method comprising administering to the patient an [$^{18}$F]-radiotracer obtained by the method of the invention, and then obtaining an image of the patient by detecting the presence in the patient's body of the [$^{18}$F]-labelled-radiotracer using PET imaging. Said method forms a further aspect of the present invention.

Conveniently, the iodonium salt solution of the method of the invention can be provided as part of a kit suitable for carrying out the method of the invention. Said kit forms a further aspect of the present invention and comprises the iodonium salt solution in a storage container, as defined above for the method of the invention. A kit is particularly convenient when the fluorine-labelled compound is a $^{18}$F-labelled compound such as a [$^{18}$F]-labelled-radiotracer, wherein said kit is suitable for preparation of said $^{18}$F-labelled compound at a radiopharmacy, PET centre, or nuclear medicine department. The kit may contain a cartridge which can be plugged into a suitably adapted automated synthesiser, described in more detail below. The kit preferably includes means for fluorinating with fluoride ion and may also comprise a column to remove unwanted fluoride ion. The reagents, solvents and other consumables required for the synthesis may also be included together with a data medium, such as a compact disc carrying software, which allows the synthesiser to be operated in a way to meet the end user's requirements for concentration, volumes, time of delivery etc.

Preferably, all components of the kit are disposable to minimise the possibilities of contamination between runs and to ensure sterility and quality assurance.

Preferred storage containers, [$^{18}$F]-labelled compounds, iodonium salts, free radical traps, organic solvents and fluoride ion sources for the kit are as defined above in relation to the method of the invention.

As alluded to above, the fluoridation method of the invention can be automated, and this is a preferred embodiment of the method of the invention, particularly for radiofluoridation. [$^{18}$F]-radiotracers are now often conveniently prepared on an automated radiosynthesis apparatus. There are several commercially-available examples of such apparatus, including Tracerlab MX and Tracerlab FX (both available from GE Healthcare). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps.

The iodonium salt solution in its storage container as described herein may be housed in such a disposable or removable cassette designed for use with an automated synthesis apparatus. Therefore, in another aspect, the present invention further provides a cassette for an automated synthesis apparatus comprising the iodonium salt solution in a storage container as described hereinbefore. The cassette can be provided complete with all of the reagents required for the fluoridation reaction, except for the radiofluoride. Advantageously, the iodonium salt is provided in solution in a single vial of the cassette, wherein said vial is a storage container as described herein. A cassette for use in an automated apparatus based on currently-known methods for fluoridation of iodonium salts would require one vial for the solid iodonium salt, and another vial for the organic solvent. Therefore, the method of the present invention means that the associated cassette for automated synthesis requires fewer components than would be necessary to automate any presently-known method. Furthermore, the length of time taken to complete the automated synthesis is shortened as there is no step of dissolving the iodonium salt.

The present invention will also be understood to encompass use of the kit of the invention, or of the cassette of the invention for carrying out the method of the invention. The suitable and various preferred embodiments of the features of the kit, cassette and method of the invention are as previously described.

BRIEF DESCRIPTION OF THE EXAMPLES

Examples 1 and 2 describe fluoridation of a quinoyliodonium salt following storage of said quinoyliodonium salt for 3 and 5 days, respectively.

EXAMPLES

Abbreviations Used in the Examples

Ac: acetyl
DCM: dichloromethane
DMF: dimethylformamide
g: gram(s)
h: hour(s)
HPLC: high-performance liquid chromatography
MeOH: methanol
mL: milliliter(s)
mp: melting point
ppm: parts per million
RCP: radiochemical purity, defined as the amount of desired radioactive product as a percentage of all radioactivity.
RCY: radiochemical yield, defined as the RCP multiplied by the decay-corrected percentage of radioactivity recovered from the reaction vessel.
TEMPO: 2,2,6,6-Tetramethylpiperidine-N-Oxide
TFA: trifluoroacetic acid
THF: tetrahydrofuran
TLC: thin-layer chromatography Comparative Example 1

Fluoridation of a Quinoyliodonium Salt without Storage

Example 1(i)

3-Iodopyridine Dichloride

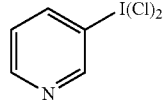

This experiment was carried out in a well ventilated fume hood. Chlorine gas was generated by drop-wise addition of concentrated hydrochloric acid on to potassium permanganate. The gas evolved was bubbled through water to remove any HCl gas, then through the reaction mixture then twice through 20% sodium hydroxide solution to destroy any unreacted chlorine. A chlorine gas detector was used throughout the experiment and was set to alarm at 0.10 ppm. The exhaust and joints were monitored for trace amounts of chlorine using wet starch paper.

Chlorine gas was bubbled slowly through a stirred solution of 3-iodopyridine (0.79 g, 5 mmol) in chloroform (150 mL) at 0° C. for 0.5 h. The resulting suspension containing a bright yellow crystalline solid was warmed to room temperature for 1 h when it was re-cooled to 0° C. and the precipitate collected by filtration and washed with hexane (50 mL) and dried in vacuo to give the title compound as a yellow crystalline solid which was used without further purification. (1.11 g, 4.85 mmol, 97%); mp 128-129° C. dec. (from CHCl$_3$).

Example 1(ii)

3-Diacetoxyiodopyridine

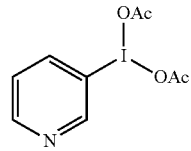 [SMILES: CC(=O)OI(OC(C)=O)c1cccnc1]

3-Iodopyridine dichloride (1.66 g, 5 mmol) was added to 10M aqueous sodium hydroxide (10 mL) solution with stirring and the suspension was stirred for 0.5 h when the solid was collected by filtration and washed with water (5 mL) and air dried for 0.5 h. The colourless solid was then added to acetic acid (5 mL) and stirred at room temperature for 0.5 h when water (30 mL) was added and the mixture was extracted with dichloromethane (2×50 mL), dried (MgSO$_4$) and concentrated in vacuo to give a yellow oil. Crystallisation gave the title compound as a colourless crystalline solid (0.36 g, 1.1 mmol, 22%); mp 104-105° C. (from DCM-ether-petrol); (Found C, 33.35; H, 3.05; N, 4.34. C$_9$H$_{10}$INO$_4$ requires C, 33.46; H, 3.12; N, 4.34%.); $v_{max}$/cm$^{-1}$ (neat) 1669, 1426, 1365, 1289, 1021, $\delta_H$ (300 MHz; CDCl$_3$) 9.17 (1H, d, H2 J 2 Hz), 8.85 (1H, d, H6 J 4 Hz), 8.42 (1H, dt, H4 J 4, 2 Hz), 7.48 (1H, d, H5 J 4 Hz), 2.03 (6H, s, COMe); $\delta_C$ (75 MHz; CDCl$_3$) 176.53 (CO), 153.78 (C2), 152.02 (C6), 142.02 (C4), 125.94 (C5), 121.02 (C3), 20.26 (COMe).

Example 1(iii)

(4-Methoxyphenyl)pyridin-3-yl-iodonium trifluoroacetate

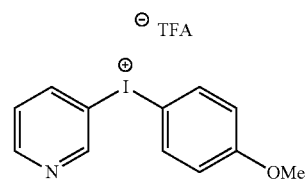 [SMILES: COc1ccc([I+]c2cccnc2)cc1]

Trifluoroacetic acid (0.15 mL, 2 mmol) was added dropwise to a stirred solution of 3-iodopyridine diacetate (0.23 g, 1 mmol) in dichloromethane at −40° C. and stirred for 0.5 h when the solution was allowed to warm to room temperature for 1 h after which time it was re-cooled to −40° C. and anisole (0.11 mL, 1 mmol) added dropwise and the reaction mixture allowed to warm to room temperature overnight. The reaction mixture was concentrated in vacuo to give a light brown oil. Crystallisation gave the title compound as a colourless crystalline solid (0.22 g, 0.52 mmol, 52%); mp 150-151° C. (from DCM-ether) silica gel TLC $R_f$ 0.20 (9:2 DCM-MeOH); (Found C, 39.67; H, 2.53; N, 3.21. $C_{14}H_{11}F_{31}NO_3$ requires C, 39.55; H, 2.61; N, 3.29%.); $v_{max}$/cm$^{-1}$ (neat) 3050, 1642, 1570, 1251, 1177, 1130; $\delta_H$ (300 MHz; $d_6$-acetone) 8.93 (1H, d, H2 J 2 Hz), 8.74 (1H, d, H6, J 4 Hz), 8.39 (1H, dt, H4 J 5, 2 Hz), 7.91 (2H, d, H2'/H6' J 5 Hz), 7.38 (1H, dd, H5 J 5, 3 Hz), 6.93 (2H, d, H3'/H5' J 5 Hz), 3.84 (3H, s, OMe); $\delta_C$ (75 MHz; $d_6$-Acetone) 163.99 (C4'), 154.59 (C2), 152.76 (C6), 143.06 (C4), 138.63 (C2'/C6'), 127.45 (C5), 118.68 (C3'/C5'), 116.64 (C1'), 107.60 (C3), 56.51 (OMe); m/z (ES) 312 (M$^+$, 100%), 185 (20). [Found: M$^+$], 311.9878.

Example 1(iv)

[$^{18}$F]-Fluoridation Method

[$^{18}$F] fluoride (typically 100-150 MBq) was transferred to the reaction vessel from a P6 vial by suction. A solution of Kryptofix® 222 (2.5 mg), 0.1M aqueous potassium carbonate (50 μL) in acetonitrile (0.5 mL) was added to the P6 vial and the solution transferred to the vessel. The solution was then dried by heating at 100° C. under a flow of nitrogen gas (0.3 L/Min) for 15 min, during which time acetonitrile aliquots (0.5 mL) were added after 5 and 7 min. The vessel was then cooled to 30° C. using compressed air when a solution of (4-Methoxyphenyl)pyridin-3-yl-iodonium trifluoroacetate (5 mg) and TEMPO (5 mg) in N,N-Dimethylformamide (0.7 mL) was added. The vessel was sealed and heated to 120° C. for 30 min when the vessel was cooled using compressed air and the mixture analysed.

In three experiments, the average radiochemical purity observed was 77%, and the average radiochemical yield was 58%.

Example 2

Fluoridation of a Quinoyliodonium Salt Following Storage for 3 Days

[$^{18}$F] fluoride was transferred to the reaction vessel from a P6 vial by suction. A solution of Kryptofix® 222 (2.5 mg, 6.6×10$^{-6}$ mols), 0.1M aqueous potassium carbonate (50 μL, 5×10$^{-6}$ mols) in acetonitrile (0.5 mL) was added to the P6 vial and the solution transferred to the vessel. The solution was then dried by heating at 100° C. under a flow of nitrogen gas (0.3 L/Min) for 15 min. The vessel was then cooled to 30° C. using compressed air when a solution of (4-Methoxyphenyl) pyridin-3-yl-iodonium trifluoroacetate (5 mg, 1.2×$^{-5}$ mols, synthesis as in Example 1) and TEMPO (5 mg, 3.2×$^{-5}$ mols) in DMF (0.7 mL) that had been stored in a refrigerator (~5° C.) for 3 days in the dark was added. The vessel was sealed and heated to 120° C. for 30 min when the vessel was cooled using compressed air. Water (0.5 mL) was added to the reaction and the mixture analysed by HPLC.

The RCP was measured by radio-HPLC. The RCY is expressed as decay-corrected and is calculated from the RCP and measured activity in the reaction vessel once the reaction is complete.

The process of storage in DMF/TEMPO increased the RCP and RCY by 11% and 5% respectively, compared with Example 1.

Example 3

Fluoridation of a Quinoyliodonium Salt Following Storage for 5 Days

[$^{18}$F] fluoride was transferred to the reaction vessel from a P6 vial by suction. A solution of Kryptofix® 222 (2.5 mg, 6.6×10$^{-6}$ mols), 0.1M aqueous potassium carbonate (50 μL, 5×10$^{-6}$ mols) in acetonitrile (0.5 mL) was added to the P6 vial and the solution transferred to the vessel. The solution was then dried by heating at 100° C. under a flow of nitrogen gas (0.3 L/Min) for 15 min. The vessel was then cooled to 30° C. using compressed air when a solution of (4-Methoxyphenyl)quinolin-3-yl-iodonium trifluoroacetate (5 mg, 1.1×$^{-5}$ mols, synthesis as in Example 1) and TEMPO (5 mg, 3.2×$^{-5}$ mols) in DMF (0.7 mL) that had been stored in a refrigerator (~5° C.) for 3 days in the dark was added. The vessel was sealed and heated to 120° C. for 30 min when the vessel was cooled using compressed air. Water (0.5 mL) was added to the reaction and the mixture analysed by HPLC.

The RCP was measured by radio-HPLC. The RCY is expressed as decay-corrected and is calculated from the RCP and measured activity in the reaction vessel once the reaction is complete.

The process of storage in DMF/TEMPO increased the RCP and RCY by 9% and 3% respectively, compared with Example 1.

What is claimed is:

1. A method for the synthesis of a fluorine-labelled compound, said method comprising:
   (a) providing an iodonium salt solution, wherein said solution comprises (i) an iodonium salt, or a protected version thereof and, (ii) a free radical trap, wherein (i) and (ii) are dissolved in an organic solvent;
   (b) storing said solution of step (a) in a storage container for a storage period between 1-7 days, at a storage temperature which is above the freezing point of said solution and which is less than or equal to 30° C.;
   (c) following said storing step (b), treating said solution with a fluoride ion source to generate said fluorine-labelled compound.

2. The method of claim 1 wherein said iodonium salt is a compound of Formula I:

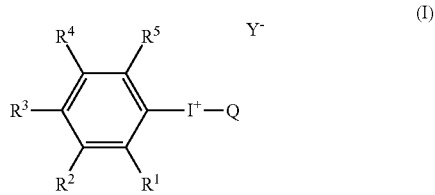

wherein:
each of $R^1$-$R^5$ is an R group independently selected from hydrogen, nitro, cyano, halo, $C_{1-10}$ hydroxyalkyl, $C_{2-10}$ carboxyalkyl, $C_{1-10}$ alkyl, $C_{2-10}$ alkoxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{2-10}$ alkenyl, $C_{2-10}$ alkynyl, $C_{1-10}$ acyl, $C_{7-10}$ aroyl, $C_{2-10}$ carboalkoxy, $C_{2-10}$ carbamoyl, or $C_{2-10}$ carbamyl, or protected versions of any of these groups; or two adjacent R groups, together with the carbon atoms to which they are attached, form a four- to six-membered ring, or protected versions thereof;

Q represents either a $C_{5-14}$ aryl, or a $C_{4-13}$ heteroaryl group, optionally attached to $I^+$ via a $C_{2-6}$ alkenylene group, wherein Q has 0 to 3 $R^6$ substituents, wherein each $R^6$ is an R* group selected from:

halo, cyano, nitro, —C(═O), -E, —OE, —OC(O)E, —C(═O)OE, —SO$_2$E, —SE, —NE$_2$, —C(═O)NE$_2$, —N(E)COE; wherein E at each occurrence is selected from hydrogen, $C_{1-6}$ alkyl, $C_{1-5}$ heteroalkyl, $C_{2-6}$ alkenyl, $C_{2-6}$ alkynyl, $C_{1-6}$ alkoxyalkyl, $C_{1-6}$ haloalkyl, $C_{2-6}$ haloalkenyl, $C_{2-6}$ haloalkynyl, $C_{1-6}$ haloalkoxy-$C_{1-6}$ alkyl, $C_{4-12}$ cycloalkyl, $C_{4-12}$ heterocycloalkyl, $C_{5-12}$ aryl, and a $C_{4-13}$ heteroaryl group;

and protected versions of any of these R* groups;

with the proviso that R* is not hydrogen;

wherein any two adjacent hydrocarbyl R* groups together with the carbons to which they are attached may form a 4- to 6-membered ring;

and wherein any of these R* groups may be attached to Q via $C_{1-6}$ alkylene;

and wherein any hydrocarbyl $R^6$ group is optionally substituted by one or more $R^7$ groups, and any hydrocarbyl $R^7$ group is optionally substituted with one or more $R^8$ groups, wherein $R^7$ and $R^8$ are both an R* group; and, $Y^-$ is an anion, suitably selected from trifluoromethane sulphonate (triflate), methane sulphonate (mesylate), trifluoroacetate, toluene sulphonate (tosylate) and perfluoro $C_2$-$C_{10}$ alkyl sulphonate.

3. The method of claim 1 wherein said iodonium salt is a compound of Formula Ia:

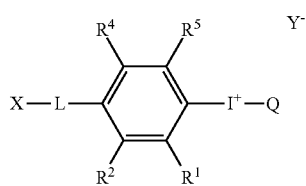

(Ia)

wherein:

$R^1$, $R^2$, $R^4$, $R^5$, and Q are as defined in claim 2 for Formula I;

L is a polyethylene glycol linker, or L comprises one to four $C_{5-12}$ arylene groups and/or $C_{1-20}$ alkylene, $C_{2-20}$ alkoxyalkylene or $C_{1-20}$ haloalkylene, and optionally one or more additional substituents such as C(═O), halogen, amide or sulphonamide; and, X is any suitable solid-phase support which is insoluble in solvents used in the method and to which the linker L is covalently bound.

4. The method of claim 1 wherein said free radical trap is selected from 4-aminobenzoic acid, 2,6-di-tert-butyl-4-methylphenol (BHT), 1,2-diphenylethylene (DPE), galvinoxyl, gentisic acid, hydroquinone, 2,2,6,6-Tetramethylpiperidine-N-Oxide (TEMPO), thiophenol, ascorbate, para-amino benzoic acid (PABA), β-carotene and DL-α-tocopherol.

5. The method of claim 1 wherein said free radical trap is present in said solution at a concentration of at least 1 mole percent.

6. The method of claim 1 wherein said organic solvent is selected from acetonitrile (ACN), dimethylformamide (DMF), dimethylsulphoxide (DMSO), dimethylacetamide (DMAC), tetrahydrofuran (THF), dioxan, 1,2 dimethoxyethane (DME), sulpholane, or N-methylpyrrolidininone.

7. The method of claim 1 wherein said storage temperature is between 1-5° C.

8. The method of claim 1 wherein said storage container is a liquid-tight or gas-tight jar, flask, ampoule or vial, wherein the seal is provided by a liquid-tight or gas-tight closure such as a lid, stopper, or septum.

9. The method of claim 1 wherein said fluoride ion source is selected from potassium fluoride, caesium fluoride and tetraalkylammonium fluoride.

10. The method of claim 1 wherein said fluorine-labelled compound is an $^{18}$F-labelled compound.

11. The method of claim 10 further comprising one or more of the following steps in any order:

(i) removal of excess $^{18}$F$^-$, for example by ion-exchange chromatography; and/or, (ii) removal of any protecting groups; and/or, (iii) removal of organic solvent; and/or, (iv) formulation of the resultant [$^{18}$F]-labelled compound as an aqueous solution; and/or, (v) sterilisation of the formulation of step (iv).

12. The method of claim 1 wherein said treating step is carried out on an automated synthesis apparatus.

13. The method of claim 11 wherein said treating step and one or more of said following steps are carried out on an automated synthesis apparatus.

* * * * *